(12) United States Patent
Delbaere

(10) Patent No.: US 10,258,659 B2
(45) Date of Patent: Apr. 16, 2019

(54) WATER SOLUBLE DEFRUCTOSYLATED PEA EXTRACT, AND USE THEREOF AS A PREBIOTIC AGENT

(71) Applicant: OLYGOSE, Venette (FR)

(72) Inventor: Francois Delbaere, Sauzon (FR)

(73) Assignee: OLYGOSE, Venette (FR)

(*) Notice: Subject to any disclaimer, the term of this patent is extended or adjusted under 35 U.S.C. 154(b) by 733 days.

(21) Appl. No.: 14/625,134

(22) Filed: Feb. 18, 2015

(65) Prior Publication Data

US 2015/0157676 A1 Jun. 11, 2015

Related U.S. Application Data

(62) Division of application No. 13/260,450, filed as application No. PCT/FR2010/000238 on Mar. 22, 2010, now Pat. No. 9,017,741.

(30) Foreign Application Priority Data

Mar. 27, 2009 (FR) ...................................... 09 01511

(51) Int. Cl.
*A61K 36/48* (2006.01)
*A61K 36/00* (2006.01)
*A23L 11/00* (2016.01)
*A23L 33/22* (2016.01)

(52) U.S. Cl.
CPC .............. *A61K 36/48* (2013.01); *A23L 11/09* (2016.08); *A23L 33/22* (2016.08); *A23V 2002/00* (2013.01); *Y02A 50/473* (2018.01)

(58) Field of Classification Search
None
See application file for complete search history.

(56) References Cited

U.S. PATENT DOCUMENTS

| 4,216,235 A | 8/1980 | Dasek et al. |
| 2008/0226810 A1 | 9/2008 | Passe et al. |
| 2009/0110651 A1* | 4/2009 | Moussou ................. A61K 8/60 |
| | | 424/62 |

FOREIGN PATENT DOCUMENTS

| CA | 2299457 A1 | 2/1999 |
| FR | 2 897 239 A1 | 8/2007 |
| JP | S54-98355 A | 8/1979 |
| JP | H04-218362 A | 8/1992 |
| JP | 2004-057043 A | 2/2004 |
| WO | 2007/017572 A1 | 2/2007 |

OTHER PUBLICATIONS

Troszynska, Agnieszka; "Antioxidant Activity of Pea (*Pisum sativum* L.) Seed Coat Acetone Extract"; Lebensm-Wiss. u-Technol., 35, 158-164 (2002).
Oki et al., "Production of Vinegar from Soybean Oligosaccharides, in vitro and in vivo Effects of the Vinegar on Human Fecal Microflora," Nippon Nogeikagaku Kaishi, 1992, vol. 66, No. 4, pp. 727-732.
Masai, Teruhisa, "The Food Industry", Aug. 30, 1987, vol. 30, No. 16, pp. 31-39.
Canadian Examination Search Report for Application No. 2,757,067 dated Apr. 25, 2016.

* cited by examiner

*Primary Examiner* — Christopher R Tate
*Assistant Examiner* — Randall Winston
(74) *Attorney, Agent, or Firm* — Sughrue Mion, PLLC

(57) ABSTRACT

The present invention relates to a water-soluble defructosylated pea extract, substantially free of proteins and peptides, as well as to an oligosaccharide composition such as that contained in said extract. It also relates to the method for preparing the same, and to the use thereof as a prebiotic agent.

19 Claims, No Drawings

WATER SOLUBLE DEFRUCTOSYLATED PEA EXTRACT, AND USE THEREOF AS A PREBIOTIC AGENT

CROSS REFERENCE TO RELATED APPLICATIONS

This application is a Divisional of U.S. application Ser. No. 13/260,450 filed Feb. 2, 2012, which is a National Stage of International Application No. PCT/FR2010/000238 filed Mar. 22, 2010, claiming benefit to French Patent Application No. 09/01511 filed Mar. 27, 2009, the contents of all of which are incorporated herein by reference in their entirety.

The present invention relates to a water-soluble defructosylated pea extract, substantially free of proteins and peptides, as well as to an oligosaccharide composition such as that contained in said extract. The invention also relates to the method for preparing the same, and to the use thereof as a prebiotic agent.

Legumes constitute a choice raw material for the agroprocessing industry, particularly for the production of proteins, starch, particularly amylose-rich starch, fibers and starch derivatives such as glucose syrups, maltodextrin, dextrose or isoglucose.

These products find outlets in varied fields, such as the adhesive or paper sectors, and especially in the food sector whereby the nutritional value of the legumes, for human consumption as much as for animal feeding, no longer has to be proven. Among the legumes, grain legumes such as beans, peas, and fava beans, are widely used for their energy and protein content. The grains of dried peas are indeed rich in carbohydrates, formed essentially of starch as well as of saccharose and oligosaccharides, in proteins (with a high lysine content) and in fibers.

In exchange for their nutritional benefits, the legumes such as dried peas have a low digestibility, which often requires soaking them in an acidic medium before they can be cooked and eaten. This drawback is mainly due to their significant content of α-galactosyl oligosaccharides constituted of units of D-galactose, D-glucose and D-fructose. Indeed, these oligosaccharides, which cannot be digested by human enzymes (incapable of degrading their α-1,6-galactosidic and β-1-4 fructosidic bonds), are transported intact up to the colon where they provide a substrate for the fermentation of bacteria such as *Clostridium perfringens*, causing flatulence. This phenomenon, according to some authors, in the case of beans (*Phaseolus vulgaris*), has been attributed, in particular, to the fructose terminal motif of the raffinose which they contain (MYHARA R M et al., *Can. Inst. Food Sci. Technol. J.*, Vol. 21, n° 3, pp. 245-250, 1988).

These oligosaccharides are thus generally eliminated either by way of agronomic lineage selection (particularly soybean or bean) low in [ . . . ] such as oligosaccharides (BURBANO C. et al., J. Sci. Food Agric., Vol. 79, pp. 1468-1472, 1999), or by separation and physical elimination, or else by enzymatic hydrolysis (by means of an α-galactosidase) or fermentative hydrolysis, carried out, in general, before the consumption of these legumes, but also by taking food supplements constituted of enzymes adapted to hydrolyze these oligosaccharides into digestible compounds, before they reach the colon (U.S. Pat. No. 5,651,967).

Document U.S. Pat. No. 4,008,334 thus proposes a method for eliminating the soluble carbohydrates from the vegetable proteins originating, in particular, from soybean, including raffinose and stachyose, by enzyme digesting by means of baker's yeast. Similarly, document U.S. Pat. No. 4,216,235 suggests using a *Saccharomyces uvarum* yeast to degrade the oligosaccharides of soybeans, including melibiose and manninotriose.

In the case of the pea, the oligosaccharides are most often eliminated during the commercial transformation of the legume grains. It is estimated that, currently, the volume of oligosaccharides generated by the refining of peas is experiencing a strong growth and is greater than 25,000 metric tons per year in Europe and in Canada. To avoid having to eliminate them in a purification plant, and thus, in spite of their low digestibility, the latter are generally handed off to farmers to be used as livestock feed. However, this solution has a high energy cost since, because of the substantial dilution of the soluble extract originating from the refining, it is necessary to concentrate it to ensure its preservation and enable its transportation and its use by animals.

It would thus be interesting to be able to have a means that would make it possible to valorize these by-products.

With that in mind, document US 2004/0198965 suggested to use oligosaccharides, present, in particular, in soybean seeds, for the synthesis of D-galactose.

The invention relates to another use of these by-products. Indeed, the Applicant has discovered that a pea soluble fraction, substantially free of proteins and peptides and rich in oligosaccharides, could, after defructosylation of the oligosaccharides, be usefully used as prebiotic agent.

The term "prebiotic" is to be understood as a non-digestible, selectively fermented food component which causes specific changes to the composition and/or activity of the intestinal microbiota, beneficial to the health and well-being of the host (Gibson G R et al., Nutrition Research Reviews, 17: 259-275, 2004). The prebiotic can in particular be considered as an aliment for favorable bacteria of the colon, such as the bifidobacteria and the lactobacilli, which enable preventing intestinal disorders, enhancing the absorption of minerals, modulating the lipid metabolism, and/or stimulating the immune system.

Since it has been discovered that it was possible to modulate the balance of the intestinal microbiota by ingesting food ingredients, numerous candidates to the appellation "prebiotic" have been studied. Most are carbohydrates of vegetable origin. The most known and the better characterized are the fructans, fructose polymers, among which are the inulin, generally extracted from chicory tubers, but also from agave, and the fructo-oligosaccharides (FOS) produced either by hydrolysis of inulin, or by biosynthesis from saccharose and fructose.

Other oligosaccharides also have prebiotic properties that are more or less established: the galacto-oligosaccharides (GOS) or "trans-galacto-oligosaccharides" (TOS), very close to the compounds present in mother's milk, the soy oligosaccharides (SOS), the isomalto-oligosaccharides (IMOS), the lactulose, the raffinose, the xylo-oligosaccharides, etc.

In spite of the numerous studies carried out on the already well characterizes prebiotics (such as the FOS and the GOS) as well as on a great number of candidate molecules, there is still, to this day, a lack of a prebiotic combining the following properties which are sought after by the (potential) producers of food and drinks with a health functionality: a simple and economical production method, very good intestinal tolerance allowing for the use of adequate concentrations to obtain, in practice, the desired results, and high stability to heating processes and to the conventional acidic media of large sectors of the food industry.

Thus, the inulins and FOS have an average intestinal tolerance. According to certain authors, symptoms of discomfort with the FOS arise as low as 2.5 g/day for 25% of the subjects, and affect 75% of the subjects at 20 g/d. The tolerance to inulins is comparable to that of the FOS, but their effective dosage to obtain a bifidogenic effect is higher, which intensifies the arbitration problem between a minimum dosage to obtain a bifidogenic effect and a maximum dosage to prevent the problems of intestinal tolerance. Furthermore, the inulins and the FOS are not stable to acids and heat.

This is not the case for the XOS, the raffinose, and the SOS which, in addition, provide good prebiotic activity. However, the latter have a very low intestinal tolerance.

Pyrodextrins, IMOS, and polydextrose, which present a good stability to acids and heat and a good tolerance, have, on the other hand, a low efficiency because of a low prebiotic specificity (their stimulation of colic bacteria is undifferentiated) and/or low indigestibility.

For their part, the GOS have an intestinal tolerance and a high stability to acidity and to processes. They are obtained by reaction of trans-galactosylation (polymerization) from lactose by means of β-galactosidases. The reaction yield is low, negatively impacted by the synthesis of the desired compounds (β-GOS), which means that various technologies for separation, particularly membrane or chromatographic, are required on the reaction product to make it possible to maintain conditions that are favorable to the trans-galactosylation and to achieve a product that is sufficiently pure for prebiotic use. These technologies are costly and thus counter to affordability of GOS prebiotics.

This results in the existing prebiotics being used only in a limited number of food applications (humanized milk in particular) and at concentrations which do not always make it possible to guarantee the effects theoretically possible according in vitro/vivo, or even clinical research.

However, the Applicant has demonstrated that oligosaccharide mixtures present in defructosylated pea extracts make it possible to achieve the desired compromise of properties for prebiotics.

The object of the present invention is thus a water-soluble pea extract substantially free of proteins and peptides and defructosylated.

It also has as an object a composition having the oligosaccharide profile of these water-soluble defructosylated pea extracts and which holds, and preferably is mostly constituted of, melibiose, manninotriose, and mannino-tetraose with a weight ratio mannino-tetraose/melibiose of at least 1:1 and preferably of at least 4:1 or even of at least 5:1 (and a maximum of about 10:1, for example) and/or a weight ratio manninotriose/mannino-tetraose of 0.3:1 to 4:1, preferably of 0.8:1 to 1:1.

It also has as an object the use as prebiotic agent of either a water-soluble defructosylated pea extract substantially free of proteins and peptides and defructosylated, or the aforementioned composition.

What is meant by "substantially free of proteins and peptides" is that the water-soluble extract according to the invention holds less than 5% in weight (dry matter) of such constituents. The latter include, in particular, the albumines.

The defructolysated pea extract according to the invention can be obtained by defructosylating the oligosaccharides present in the solubles of peas substantially free of proteins and peptides.

The method for obtaining this extract can in particular comprise the following steps:
1—Separation of the flocculatable proteins, insoluble fibers and/or starch of the pea or pea flour to obtain a water-soluble pea extract,
2—Elimination of the soluble peptides, in particular of the antitrypsic factors,
3—Action of an invertase, originating, for example, from *Saccharomyces cerevisiae*, on said extract, under conditions allowing for the defructosylation of the oligosaccharides present in said extract, and
4—Recovery of the defructosylated extract thus obtained.

The invention thus also has as an object a method for preparing a water-soluble defructosylated pea extract substantially free of proteins and peptides comprising at least the successive steps described hereinabove.

It must be understood that this method can, as explained below, comprise other preliminary, intermediary or subsequent steps to those indicated hereinabove. Thus, it can also include at least one demineralization (desalting) steps to reduce the reactions of coloration in certain applications. Before the other minerals are eliminated, a step of elimination of the potash (by crystallization, for example) similar to that carried out on sugar vinasse, is advantageously carried out. The salts present in the pea solubles being particularly rich in potassium (on the order of 35%), this treatment has the dual advantage of reducing by about 50% the mineral content left to be eliminated by other techniques (particularly ion-exchange resins) and of generating some potash which constitutes a highly-valued fertilizer, allowed in organic agriculture. This treatment generally consists of an acidification (often with H2SO4) followed by a neutralization with ammonia, the crystals being recovered by decanting and/or centrifugation. Alternatively, membrane techniques (particularly electrodialysis) that make it possible to optimize the method while reducing costs can be used.

Such method is generally implemented on a native pea. The pea according to the invention can be a variety of smooth or wrinkled peas and is advantageously chosen from among those of the species *Pisum sativum* L., particularly among the subspecies: *elatius, transcaucasicum* Govorov, *syriacum* Berger, *abyssinicum* Govorov, *asiaticum* Govorov, *sativum* (varieties *Arvense* L., *sativum* or *macrocarpon*, for example).

The peas can be first washed, sorted, trimmed and/or dusted off before they are grinded into a flour which is then suspended in water.

The separation of the flocculatable proteins, starch and/or insoluble fibers can be done by any means known to one having ordinary skill in the art, and particularly by extraction, centrifugation, decanting, membrane filtration (particularly ultrafiltration) or isoelectric precipitation of the proteins or by a combination of several of these means, possibly combined with a concentration step, for example by reverse osmosis and/or vacuum evaporation. An example of such separation method is described in application WO 2007/017572.

The pea solubles obtained are rich in peptides and in oligosaccharides. These pea solubles are processed to separate the peptides, which have a molecular weight greater than 5,000 Da, advantageously by ultrafiltration and/or nanofiltration. It must be noted that the recoverable peptide fraction is enriched with albumin PA1b (having a molecular weight of 11,000 Da) whose insecticide properties suitable to cereals are described in application EP 1 078 085. The recovery of the fraction for such non-food use thus constitutes an additional potential advantage of the present invention.

At the end of this step, a water-soluble fraction rich in oligosaccharides and substantially free of proteins and peptides and which can advantageously by concentrated by reverse osmosis is obtained.

The defructosylation of the oligosaccharides of residual peas contained in this fraction can thus be carried out in a continuous or sequential manner, by any method of acid, thermal and/or enzyme hydrolysis allowing for eliminating the terminal fructose motif from the oligosaccharides present in the pea solubles, while preserving their α-galactosidic bonds, and in particular while subjecting them to the action of an enzyme or of yeast (advantageously *Saccharomyces cerevisiae*) having an invertase (or β-fructofuranosidase) activity. This step makes it possible to transform respectively the raffinose, the stachyose, and the verbascose into melibiose, manninotriose, and mannino-tetraose.

The free enzyme (invertase of *Saccharomyces cerevisiae*) can, for example, be implemented in a quantity of 200 to 300 $UI \cdot mg^{-1}$ dry, at a temperature of 40 to 50° C., advantageously with a pH of 5.0 to 5.4, for a duration comprised, for example, between 10 to 14 h, on an ultrafiltrate concentrated at 100-400 g/l, for example at about 200 g/l, in a proportion of 50 to 70 UI of enzyme per gram of dry matter of the ultrafiltrate.

The use of yeast rather than an enzyme in this defructosylation method presents the advantage that the yeast uses, and thus eliminates, the fructose produced by the reaction, which makes it possible to recover directly (without later separation) a product without sugar. In the case where the method according to the invention uses an enzyme, it shall comprise, on the contrary, an additional step for eliminating the fructose.

This method presents several non-negligible environmental advantages with respect to the methods for obtaining prebiotics of the prior art, insofar as:
  The raw materials that are used are preferably waste products of the agro-processing industry,
  It advantageously calls upon membrane purification techniques, which consume little energy,
  It makes it possible to have recourse to natural biotechnologies by using non-modified conventional microorganisms.

The soluble defructolysated pea extract obtained can be used in liquid form or possibly in powder form after having been dehydrated, particularly by atomization or freeze-drying. Its use in liquid form is preferred since, due to its low average molecular weight and to its polydispersity, the product provides a low viscosity, does not cause crystallization problems and provides good microbiological stability.

It has been demonstrated that the oligosaccharide profile of the defructosylated pea is particularly advantageous in terms of the sought after prebiotic efficiency and of its tolerance with respect to oligosaccharide mixtures originating from other defructosylated legumes, such as soybeans or beans. In particular, the laxative effect of the pea is less than that of the soybean and it has prebiotic effects not only at the entrance of the colon, but also in the proximal and median colon. Furthermore, the defructosylation method is less complex and costly in the case of the pea than with other legumes such as soybeans or beans, insofar as it does not require a step of separating the sucrose or of demineralization, which, on the other hand, is indispensable in the case of soybeans, whose solubles are very rich in mineral salts.

In addition, because of the elimination of the fructose, the defructosylated pea extract according to the invention is hypocariogenic and has a low caloric value.

The defructosylated pea extract according to the invention and the similar compositions thus constitute a prebiotic ingredient of choice in view of at least one of the following benefits being obtained: modification of the bacterial composition of the colon, stimulation of the bifidobacteria and lactobacilli, diminution of the relative quantity of harmful bacteria and pathogenic germs such as *Clostridium, E. coli*, diminution of the luminal pH, increase of mineral absorption, in particular of calcium, stimulation of detoxifying bacterial enzymes, repression of toxifying bacterial enzymes, insolubilization of the bile slats enhancing their excretion, inhibition of the biliary acid conversion, diminution of the production of harmful compounds such as phenols and indoles, diminution of constipation, decreased risk of infectious diarrheas, decrease of inflammatory bowel diseases, stimulation of the production of short-chain fatty acids, stimulation of the apoptosis, prevention of colon cancer, reinforcement of the intestinal barrier, diminution of the bacterial translocation and/or of bacterial toxins, stimulation of the secretion of satiation hormones, diminution of the cholesterol level, weight reduction, diminution of weight gain, diminution of food intake, adipogenesis reduction and/or reduction of the symptoms of metabolic irregularity.

They are thus advantageously used to these ends, or for the fabrication of a composition adapted to obtain at least one of the aforementioned benefits.

In addition, because it is easy to obtain and inexpensive to manufacture, the defructosylated pea extract according to the invention is well-suited for use in consumer market products. It is particularly well-adapted for use in shelf-stable products and sweet carbonated drinks because of its stability in storage, heat, and acids.

In these applications, the defructosylation of the pea extract can be carried out before its incorporation with a food product or drink to which it is intended to provide prebiotic properties. Alternatively, the defructosylation can be carried out during the preparation treatment and/or during storage (under the action of the acidity or invertase activity present in such food product or in such drink).

The present invention thus has as an object a carbonated drink having at least one sweetener and one water-soluble defructosylated pea extract and/or a composition such as previously described.

It also has for an object a food such as a shelf-stable food, a yogurt or baby milk containing a water-soluble defructosylated pea extract and/or a composition such as previously described.

Alternatively, the defructosylated pea extract according to the invention, or the corresponding composition, can be administered as a nutritional supplement, for example in the form of syrup, capsule, tablet, powder for oral suspension, or any other galenic form adapted to oral administration.

According to an embodiment of the invention, the drink, the food, or the nutritional supplement containing the defructosylated pea extract according to the invention, or the corresponding composition, can also include at least one other prebiotic agent, particularly originating from defructosylated soybean solubles, defructosylated fava bean, or defructosylated beetroot vinasses.

The invention will now be illustrated by way of the non-limiting examples that follow.

EXAMPLES

Example 1: Preparation of a Water-Soluble Defructosylated Pea Extract

A pea water-soluble fraction, at 50% weight of dry matter obtained after extraction of the starch and fibers and coagulation of the proteins, is diluted at 15% weight of thy matter and filtered by means of an ultrafiltration membrane, with a cutoff fixed at 5,000 Da, so as to clarify it and remove the peptides from it. This step is followed by a concentration of the ultrafiltrate by reverse osmosis, to bring it back to 20% weight of dry matter.

At the same time, 100 ml of a solution of invertase at 1 mg/ml is prepared and subsequently washed by centrifugation for 30 minutes. The pellet is collected from 50 ml of water. An amount of 980 ml of the pea fraction is then mixed with 50 ml of the enzyme solution in a double-wall reactor with agitator placed in a water bath at 50° C. The hydrolysis is controlled by dosage of the reducing sugars by means of an aqueous alkaline solution of 3.5-dinitrosalicylic acid (DNS), at different time intervals. After at least 12 h of hydrolysis, the enzyme is neutralized, then the product obtained is centrifuged then filtered to obtain a clear solution which is then concentrated by vacuum rotary evaporation at 70° C. until a clear juice is obtained.

Example 2: Study of Digestive Tolerance of the Water-Soluble Defructosylated Pea Extract 2-1: Objective of the Study The objective of this study was to compare the digestive tolerance of the product originating from the present invention (defructolysated oligosaccharides: DO) to that of two prebiotics already on the market and to that of a placebo.

This study of digestive tolerance has been carried out in France on 17 volunteers (8 men and 9 women), double-blind.

2-2: Test Procedure

The volunteers having participated in this study have consumed, in a random manner, 20 g of active substance diluted in orange juice in one dose, each dose being spaced apart by a 48-hour rest period, to achieve four doses, total.

The different products tested were:
 defructosylated oligosaccharides (DO: product of the invention),
 β-galacto-oligosaccharides (β-GOS),
 fructo-oligosaccharides (FOS),
 saccharose (placebo)

The digestive tolerance was evaluated by means of a questionnaire reporting on the frequency (graded from 1: no symptom to 5: very frequent symptoms) and the intensity (graded from 1: no symptom felt to 5: substantial and/or unacceptable symptoms) from 6 different parameters:
 abdominal pain,
 bloating,
 abdominal noises (borborygmi, gurgling sounds . . . ),
 flatulence,
 nausea, regurgitation or heartburn,
 need to defecate 2-3: Results and Conclusions of the Study The results of the study are presented in Table 1 herein below, which regroups the average grades obtained for each parameter subsequent to the evaluation of digestive tolerance of DOs, β-GOS, and FOS compared to that of a placebo.

TABLE 1

|  | Abdominal pain | | Bloating | | Abdominal noises | | Flatulence | | Nausea | | Need to defecate | | Cumulative |
| --- | --- | --- | --- | --- | --- | --- | --- | --- | --- | --- | --- | --- | --- |
|  | F | I | F | I | F | I | F | I | F | I | F | I | grade |
| placebo | $1.1^a$ | $1.1^a$ | $1.2^a$ | $1.2^a$ | $1.2^a$ | $1.2^a$ | $1.9^a$ | $1.5^a$ | $1.0^a$ | $1.0^a$ | $1.6^a$ | $1.2^a$ | $15.1^a$ |
| DO | $1.4^a$ | $1.4^a$ | $1.9^b$ | $1.5^{ab}$ | $2.0^b$ | $1.8^b$ | $3.1^b$ | $2.6^b$ | $1.2^a$ | $1.2^a$ | $2.0^a$ | $1.8^a$ | $21.9^b$ |
| β-GOS | $1.6^{ab}$ | $1.5^{ab}$ | $1.6^{ab}$ | $1.7^b$ | $1.8^b$ | $1.6^{ab}$ | $2.9^b$ | $2.5^b$ | $1.2^a$ | $1.1^a$ | $2.1^a$ | $1.7^a$ | $21.3^b$ |
| FOS | $2.0^b$ | $1.9^b$ | $2.1^b$ | $1.9^b$ | $2.1^b$ | $2.0^b$ | $3.2^b$ | $2.7^b$ | $1.0^a$ | $1.0^a$ | $2.1^a$ | $2.1^a$ | $24.2^b$ |

F: frequency of the symptoms;
I: intensity of the symptoms.
$a,b$: values of the products having a different letter are significantly different from the other values ($p < 0.05$; Duncan's differentiation test)

It emerges from Table 1 that the frequency and severity of the symptoms observed from the consumption of the different products tested have shown that the latter did not cause digestive intolerance (cumulative grades about equal to the third of the maximum grade).

However, certain differences between products have been observed:
 the DOs were as well tolerated as the β-GOS (product having the best tolerance among the prebiotics currently on the market) compared to the placebo (which has the lowest grades for all the symptoms)
 the DOs have shown better digestive tolerance than the FOS (which remains the product that is the least well-tolerated with the highest grades for all the symptoms).

This study thus demonstrates the satisfactory digestive tolerance of the product originating from the invention.

Example 3: Study of the Bifidogenic Effect of the Water-Soluble Defructosylated Pea Extract To evaluate the bifidogenic effect of the extract according to the invention on the intestinal microbiota, a randomized, monocentric, double-blind, placebo-controlled study was carried on 36 healthy volunteers (men and women from 20 to 45-years old) distributed into two equal groups, as out-patients. The product according to the invention was consumed at a dose of 7 g of oligosaccharides (representing 95% dry matter) per day in one dose, whereas the placebo was constituted of syrup made of dehydrated glucose consumed at the same dosage. The duration of the treatment was 3 weeks. The bifidobacteria were dosed in real-time by quantitative PCR.

Example 4: Study of Stability in Acidic Medium of the Water-Soluble Defructosylated Pea Extract The stability in acidic medium of the defructosylated pea extract according to the invention was evaluated on sugar-free cola-type drinks having a pH of 2.8. The tests were carried out in comparison with an identical but not defructosylated pea extract.

To this end, half of the bottles of each of these lots, containing 2.48 g of the tested extract, was stored at ambient temperature and the other half was stored at 37° C., for one month.

Samples of each lot kept at each temperature were collected twice a week. The samples were analyzed by HPLC in order to determine the variation of their concentration in oligosaccharides over time, and thus, the stability of the latter.

The invention claimed is:

1. A water-soluble defructosylated pea extract, wherein said water-soluble defructosylated pea extract is substantially free of proteins and peptides,
   wherein said water-soluble defructosylated pea extract comprises melibiose, manninotriose and mannino-tetraose, and
   wherein said water-soluble defructosylated pea extract is obtained by a method comprising successive steps of:
      separating flocculatable proteins, insoluble fibers, and/or starch of a pea flour to obtain a water-soluble pea extract,
      eliminating soluble peptides in the water-soluble pea extract,
      contacting said water-soluble pea extract with an invertase under conditions allowing for defructosylation of oligosaccharides present in said water-soluble pea extract, thereby forming a water-soluble defructosylated pea extract, and
      recovering of the water-soluble defructosylated pea extract thus obtained.

2. The water-soluble defructosylated pea extract according to claim 1, wherein the water-soluble defructosylated pea extract is obtained from peas chosen from those of the species *Pisum sativum* L.

3. The water-soluble defructosylated pea extract according to claim 1, wherein said water-soluble defructosylated pea extract consists essentially of melibiose, manninotriose and mannino-tetraose.

4. The water-soluble defructosylated pea extract according to claim 1, wherein said water-soluble defructosylated pea extract comprises melibiose, manninotriose, and mannino-tetraose with a weight ratio mannino-tetraose/melibiose of at least 1:1 and/or a weight ratio manninotriose/mannino-tetraose of 0.3:1 to 4:1.

5. The water-soluble defructosylated pea extract according to claim 1, wherein the weight ratio mannino-tetraose/melibiose is at least 4:1.

6. The water-soluble defructosylated pea extract according to claim 1, wherein the weight ratio mannino-tetraose/melibiose is at least 5:1.

7. The water-soluble defructosylated pea extract according to claim 1, wherein the weight ratio of manninotriose/mannino-tetraose is 0.8:1 to 1:1.

8. The water-soluble defructosylated pea extract according to claim 1, wherein the weight ratio mannino-tetraose/melibiose is at least 4:1 and the weight ratio manninotriose/mannino-tetraose is 0.8:1 to 1:1.

9. The water-soluble defructosylated pea extract according to claim 1, wherein the weight ratio mannino-tetraose/melibiose is at least 5:1 and the weight ratio manninotriose/mannino-tetraose is 0.8:1 to 1:1.

10. The water-soluble defructosylated pea extract according to claim 2, wherein said peas chosen from those of the species *Pisum sativum* L. are selected from the group of subspecies consisting of *elatius, transcaucasicum* Govorov, *syriacum* Berger, *abyssinicum* Govorov, *asiaticum* Govorov, and *sativum*.

11. The water-soluble defructosylated pea extract according to claim 1, wherein the eliminating antritrypsic factors comprises elimination of antitrypsic factors.

12. A prebiotic agent containing an effective amount of the water-soluble defructosylated pea extract according to claim 1.

13. The prebiotic agent according to claim 12, wherein said prebiotic is for the modification of the bacterial composition of the colon, the stimulation of the bifidobacteria and lactobacilli, the diminution of the relative quantity of harmful bacteria and pathogenic germs such as *Clostridium, E. coli*, diminution of the luminal pH, the increase of mineral absorption, in particular of calcium, the stimulation of detoxifying bacterial enzymes, the repression of toxifying bacterial enzymes, the insolubilization of the bile slats enhancing their excretion, the inhibition of the biliary acid conversion, diminution of the production of harmful compounds such as phenols and indoles, the diminution of constipation, decreased risk of infectious diarrheas, the decrease of inflammatory bowel diseases, the stimulation of the production of short-chain fatty acids, the stimulation of the apoptosis, prevention of colon cancer, the reinforcement of the intestinal barrier, the diminution of the bacterial translocation and/or of bacterial toxins, the stimulation of the secretion of satiation hormones, the diminution of the cholesterol level, the weight reduction, the diminution of weight gain, the diminution of food intake, the adipogenesis reduction and/or the reduction of the symptoms of metabolic irregularity.

14. A carbonated drink containing at least an effective amount of sweetener and one water-soluble defructosylated pea extract according to claim 1.

15. A food containing an effective amount of water-soluble defructosylated pea extract according to claim 1.

16. The food of claim 15, wherein the food is a shelf-stable food, a yogurt, or a baby milk.

17. A method for preparing the water-soluble defructosylated pea extract according to claim 1, comprising at least successive steps of:
   separating the flocculatable proteins, insoluble fibers and/or starch of a pea flour to obtain a water-soluble pea extract,
   eliminating soluble peptides in the water-soluble pea extract,
   contacting said water-soluble pea extract with an invertase under conditions allowing for defructosylation of oligosaccharides present in said water-soluble pea extract, thereby forming a water-soluble defructosylated pea extract, and
   recovering the water-soluble defructosylated pea extract thus obtained.

18. The method of claim 17 wherein the invertase originates from *Saccharomyces cerevisiae*.

19. A method for stimulating the secretion of satiation hormones, reducing weight, diminishing weight gain, diminishing food intake or reducing adipogenesis in a subject in need thereof, said method comprising the step of administering to said subject an effective amount of the water-soluble defructosylated pea extract according to claim 1.

* * * * *